United States Patent
Sasazawa et al.

(10) Patent No.: US 8,638,430 B2
(45) Date of Patent: Jan. 28, 2014

(54) METHOD FOR DEFECT DETERMINATION IN FINE CONCAVE-CONVEX PATTERN AND METHOD FOR DEFECT DETERMINATION ON PATTERNED MEDIUM

(75) Inventors: Hideaki Sasazawa, Yokohama (JP); Takenori Hirose, Tokyo (JP); Shigeru Serikawa, Chigasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 910 days.

(21) Appl. No.: 12/789,188

(22) Filed: May 27, 2010

(65) Prior Publication Data

US 2011/0001962 A1    Jan. 6, 2011

(30) Foreign Application Priority Data

May 28, 2009   (JP) ................. 2009-128996

(51) Int. Cl.
| | | |
|---|---|---|
| *G01N 21/00* | (2006.01) | |
| *G01N 21/956* | (2006.01) | |
| *H01L 21/66* | (2006.01) | |
| *G01N 21/95* | (2006.01) | |

(52) U.S. Cl.
CPC ............ *G01N 21/956* (2013.01); *H01L 22/10* (2013.01); *G01N 21/95607* (2013.01); *G01N 21/9501* (2013.01)
USPC .................... 356/237.5; 356/237.1; 356/237.3

(58) Field of Classification Search
None
See application file for complete search history.

(56) References Cited

U.S. PATENT DOCUMENTS

| | | | | |
|---|---|---|---|---|
| 6,342,707 | B1 * | 1/2002 | Cromwell et al. | 250/559.4 |
| 6,639,663 | B1 | 10/2003 | Markle et al. | |
| 8,142,693 | B2 * | 3/2012 | Umezawa et al. | 356/237.5 |
| 2001/0000460 | A1 * | 4/2001 | Ishihara et al. | 382/149 |
| 2003/0174608 | A1 * | 9/2003 | Nakamura et al. | 369/47.26 |

FOREIGN PATENT DOCUMENTS

JP       2007-133985       5/2007

OTHER PUBLICATIONS

Raymond, Christopher J., et al., Scatterometry for shallow trench isolation (STI) process metrology; Proceedings of SPIE vol. 4344, 2001, pp. 716-725.
Minhas, Babar K. et al.; Ellipsometric scatterometry for the metrology of sub-0.1-µm-linewidth structures; Applied Optics, vol. 37, No. 22; Aug. 1, 1998; pp. 5112-5115.

* cited by examiner

*Primary Examiner* — Gregory J Toatley
*Assistant Examiner* — Juan D Valentin, II
(74) *Attorney, Agent, or Firm* — Foley & Lardner LLP

(57) ABSTRACT

In the inspection of a defect in a fine concave-convex pattern, a spectral waveform of a detection area of an inspection object is detected, area determination as to which area section determined by a pattern type of the inspection object the detection area belongs to is performed, a feature calculation equation and a determination index value which correspond to a determined area section and vary according to defect type is selected, feature calculation on the spectral waveform data in accordance with the selected feature calculation equation is performed, and a calculated feature value and the selected determination index value are compared to perform determination processing according to defect type.

12 Claims, 7 Drawing Sheets

FIG. 10
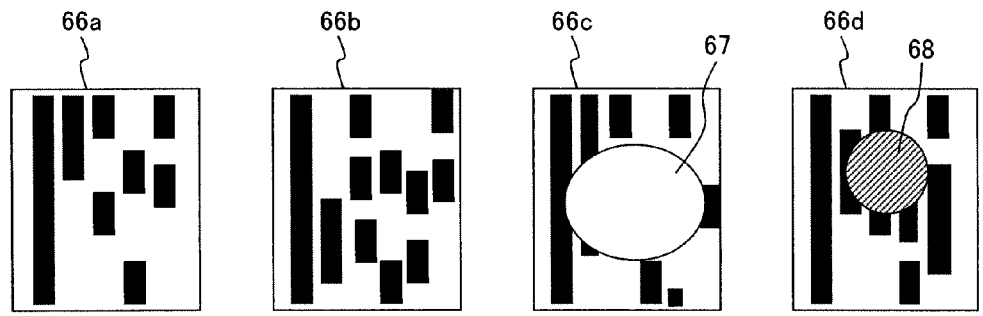
FIG. 11A
| | | | DEFECT TYPE | | |
|---|---|---|---|---|---|
| | | | MISSING | PARTICLE | SCRATCH |
| DETECTION AREA | DATA | | $F1(\lambda),Th1$ | $F2(\lambda),Th2$ | $F3(\lambda),Th3$ |
| | SERVO | ADDRESS | ... | ... | ... |
| | | CLOCK | ... | ... | ... |
| | | TRACKING | ... | ... | ... |
FIG. 11B
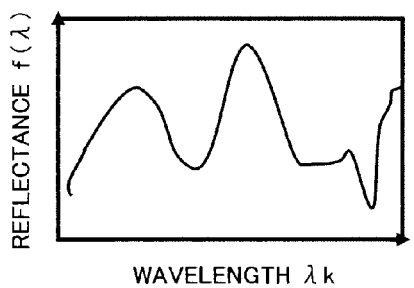

FIG. 12
|  |  |  | DEFECT TYPE | | |
|---|---|---|---|---|---|
|  |  |  | MISSING | FILLER | PARTICLE |
| DETECTION AREA | DATA | INNER PERIPHERY | F1($\lambda$),Th1 | F2($\lambda$),Th2 | F3($\lambda$),Th3 |
|  |  | MIDDLE PERIPHERY | ... | ... | ... |
|  |  | OUTER PERIPHERY | ... | ... | ... |
|  | SERVO | ADDRESS | ... | ... | ... |
|  |  | CLOCK | ... | ... | ... |
|  |  | TRACKING | ... | ... | ... |
FIG. 13A
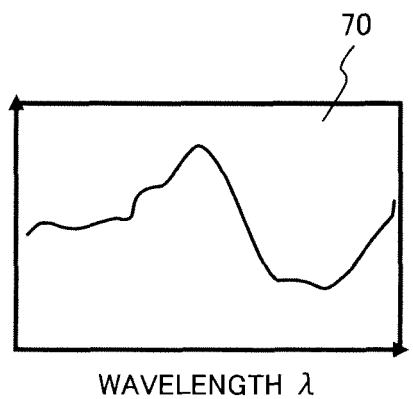
WAVELENGTH $\lambda$
FIG. 13B
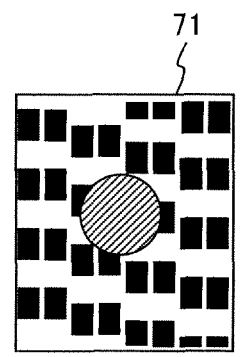

METHOD FOR DEFECT DETERMINATION IN FINE CONCAVE-CONVEX PATTERN AND METHOD FOR DEFECT DETERMINATION ON PATTERNED MEDIUM

CLAIM OF PRIORITY

The present application claims priority from Japanese patent application JP2009-128996 filed on May 28, 2009, the content of which is hereby incorporated by reference into this application.

BACKGROUND OF THE INVENTION

1. Field of the Invention

The present invention relates to inspection of a product and a process for producing a concave-convex pattern shape such as on a hard disk medium, and to a technique for inspecting a defect, deformation, and dimension measurement of the pattern shape.

2. Description of the Related Art

In recent years, hard disks as recording media for use in computers have been increasing in capacity. For increases in the capacity of recording information, it is essential to increase the recording density of a disk. As a method for greatly increasing the recording density compared to conventional disk media, patterned media having patterns formed on the disk surface are showing great promise. To form patterned media, a nanoimprint technique for forming nano-order patterns at low cost is used. In the nanoimprint technique, a prepared stamp is pressed against material to duplicate the same pattern as the stamp. With the nanoimprint technique, the formation of optical elements and an alternative to a semiconductor exposure process as well as patterned media for HDDs have been studied.

In general, pattern dimensions for use in patterned media are less than 100 nm, that is, less than the wavelengths of visible light. This exceeds the resolution limit of an optical system such as an ordinary microscope, so that the system cannot directly capture a pattern shape. Accordingly, shape measurement by an AFM, measurement by a SEM, or near-field light detection by an SNOM or the like can be considered; however, from the viewpoint of throughput, none of them makes it possible to observe a wide area at high speed.

On the other hand, in semiconductor patterning process control, an optical inspection apparatus of scatterometry theory is applied. With this, a periodic pattern such as a line-and-space pattern is detected using a control pattern called a TEG pattern disposed beforehand in an area other than a product, on a semiconductor wafer. For example, according to this method, white light is applied to a periodic pattern in an area of more than about 50 μm square, and the spectral characteristics of the reflected light are detected, so that the shape of the observation pattern is calculated. Japanese Patent Application Laid-Open No. 2007-133985 discloses a patterned media inspection according to this method. In accordance therewith, detected light reflection intensity is analyzed with the scatterometry method, thereby making it possible to measure and evaluate the shape of a periodic pattern. Further, in the case where servo information sections exist on a sample, analyzing acquired data enables similar evaluation.

U.S. Pat. No. 6,639,663 describes a method for utilizing a detection tool according to the scatterometry method to classify semiconductor defects.

The details of optical scatterometry are described in Proceedings of SPIE, Vol. 4344, pp. 716-725 (2001) and Applied Optics, Vol. 37, pp. 5112-5115 (1998). In short, light is applied to a one-dimensional periodic structure, and dependency on an incident angle, a wavelength, a polarization direction, and a reflection order in the intensity distribution of the reflected light is checked, thereby obtaining information such as the dimensions, space period, cross-section shape, and optical property of the periodic structure. According to this method, it is possible to detect a minute difference, a particle, or a defect in a periodic structure smaller than the wavelength of light.

BRIEF SUMMARY OF THE INVENTION

In a patterned medium for an HDD, patterns of data areas for recording user information and servo areas for controlling read/write positions on the disk are generally mixed. Data area patterns are periodic patterns such as a line-and-space pattern or a cylindrical pit pattern, and servo area patterns include periodicity different from data area periodicity or no periodicity. In general, there are tens to hundreds of servo areas on one disk, and they are arranged radially correspondingly to head arm tracing.

In a manufacturing process, there are various types of defects such as pattern deformation, peeling, a dent, a scratch, and a particle on the disk. Further, the acceptance or rejection of the product depends on a defective area on the disk. For example, if a minute scratch defect occurs in a data area, the data area is registered as an unusable area, thereby enabling the product to be used. On the other hand, if a similar defect occurs in an address determination pattern in a servo area, an entire data area determined by the address pattern can be unusable, which leads to a critical defect, so that the product is rejected.

In such defect determination, a conventional method, that is, the inspection of the shape of an object only with detected reflection light intensity by the scatterometry method, complicates the analysis, increases the inspection time by analysis or matching processing, and decreases the inspection/measurement accuracy.

Further, the criticality of a defect varies depending on the defective area, there has been required a method for classifying defects in accordance with characteristics of patterned media.

It is an object of the present invention to easily identify a defect type on a sample where fine concave-convex patterns are formed, without increasing inspection time.

To address the above problems, the present invention provides a method for determining a defect in a fine concave-convex pattern, including the steps of, when a feature of an inspection object is detected with a scatterometry method in inspection of a fine concave-convex pattern, detecting a spectral waveform of a detection area of the inspection object; performing area determination as to which area section determined by a pattern type of the inspection object the detection area belongs to; selecting a feature calculation equation and a determination index value which correspond to a determined area section and vary according to defect type, based on a result of the area determination; performing feature calculation on the spectral waveform data in accordance with the selected feature calculation equation; and comparing a calculated feature value with the selected determination index value to perform determination processing according to defect type.

Further, the invention provides the method for determining a defect in a fine concave-convex pattern, in which the pattern type of the inspection object is classified into a periodic pattern and a non-periodic pattern to perform area determination.

Further, the invention provides the method for determining a defect in a fine concave-convex pattern, in which with an optical signal which changes depending on the pattern type of the inspection object and the defect type, an optical signal variation of a non-defective pattern and an optical signal change caused by a defect are compared, and a significant signal change is captured, thereby performing defect determination. In this case, a wavelength of a significant change is selected to capture the significant signal change.

Further, the invention provides the method for determining a defect in a fine concave-convex pattern, in which a determination index value according to pattern type is determined with parameters which are the pattern type of the inspection object, the defect type, an optical signal variation caused by a pattern variation, and an optical signal displacement changed by a defect.

Furthermore, according to the invention, the method for determining a defect in a fine concave-convex pattern is used for the detection of a defect on a patterned medium.

In the detection of a defect on a patterned medium, the defect type includes, for example, a missing, a particle, and a scratch. Further, in the detection of a defect on a patterned medium, the area section includes, for example, a data area and a servo area. Moreover, the data area is divided into an inner periphery area, a middle periphery area, and an outer periphery area, and the servo area is divided into an address area, a clock area, and a tracking area.

The invention makes it possible to easily identify a defect type on a sample where fine concave-convex patterns are formed, such as on a patterned medium, and contributes to the stability of processes and the enhancement of yields.

BRIEF DESCRIPTION OF THE DRAWINGS

FIG. 10 is a view showing examples of the detected four locations in the address area in the servo area;

FIGS. 11A and 11B are views showing an example of a determination database table;

FIG. 12 is a view showing a determination database table according to another embodiment; and FIGS. 13A and 13B are views showing examples of a spectral waveform and a camera image thereof in a defective area.

DETAILED DESCRIPTION OF THE INVENTION

Hereinafter, description will be made on embodiments of "a method for determining a defect in a fine concave-convex pattern" according to the present invention.

First Embodiment

Figure 1:
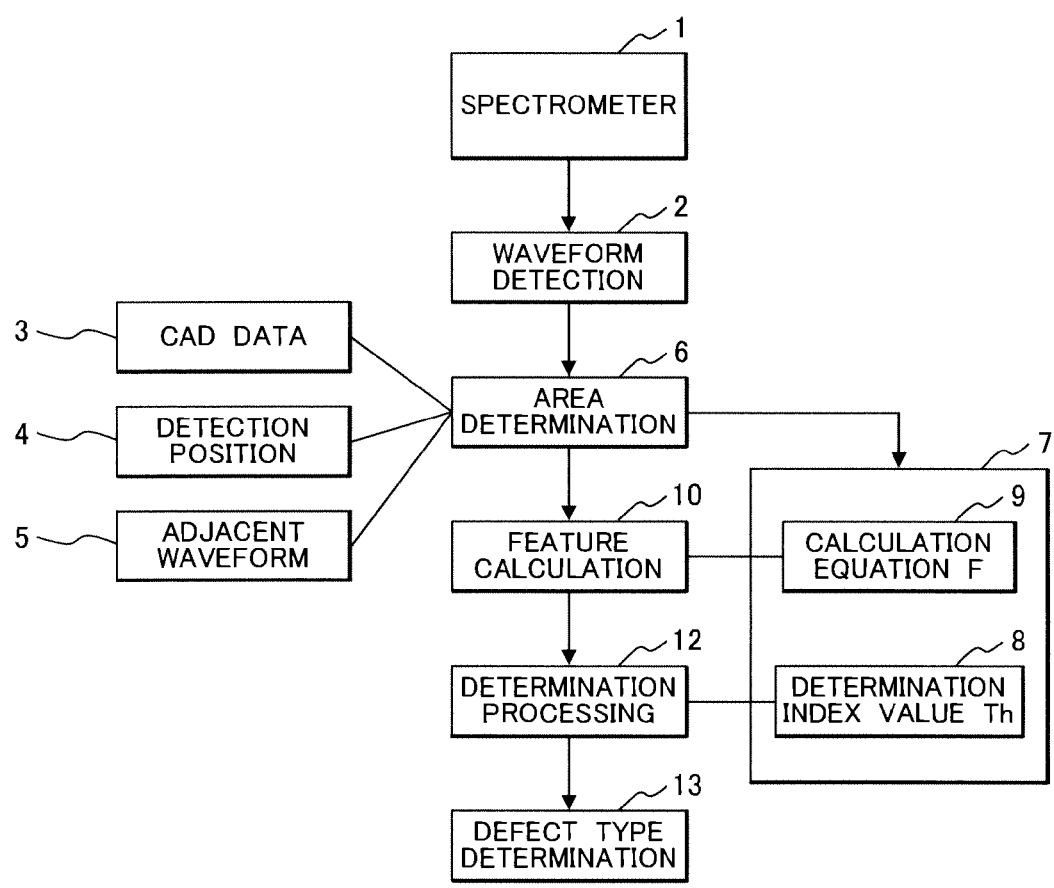
FIG. 1 is a flowchart of defect determination processing according to an embodiment of the present invention.

FIG. 1 shows a process flow of patterned media inspection according to the present invention.

A spectrometer 1 detects the spectral reflectance of a detection area on a patterned media disk to be inspected to perform waveform detection 2 as spectral waveform data. Then, based on a detection position 4 and CAD data 3 as media design information, area determination 6 is performed as to which area the detected waveform belongs to. The area refers to an area section such as a data area and a servo area determined by a pattern type on the disk. In the case where there is no alignment mark or the like necessary for positioning on the disk so that the detection position 4 is undetectable, the area determination 6 is performed in comparison with an adjacent waveform 5 associated with an area section detected beforehand.

Based on the result of the area determination 6, a calculation equation F 9 and a determination index value Th 8 corresponding to the determined area are selected from a determination database 7. In accordance with the calculation equation 9, feature calculation 10 is performed on the detected spectral waveform data. Then, in determination processing 12, the calculated feature value and the corresponding determination index value 8 are compared to perform determination processing. Lastly, defect type determination 13 is performed based on the result of the determination processing.

An inspection apparatus for performing such processing is configured, for example, as follows.

The inspection apparatus has a stage for holding, moving, and scanning a patterned media disk as a sample, an illumination optical system for applying light to the sample, a detection optical system for detecting reflected light of the applied light, an optoelectronic device for converting the detected light into an electrical signal, means for storing the detected electrical signal, means for detecting a feature from the electrical signal, means for acquiring design data such as information about pattern arrangement on the sample, position detection means for locating the position of the detected signal on the sample in comparison with the design data, means for storing reflected light from a defective disk, means for performing data classification according to a defect type and a defect location, and determination means for determining criticality based on obtained data.

The scanning stage may be an Rθ stage for rotating and scanning the sample in the radial direction or an XY stage for scanning the sample in the orthogonal direction.

The illumination optical system may be an optical system for applying white light, an optical system for applying invisible light such as ultraviolet or infrared light, an optical system using a laser light source having a specific wavelength, or an optical system for applying polarized light.

The detection optical system may be a spectral optical system for detecting white light including ultraviolet light at each wavelength or an optical system for detecting reflected light of a specific single wavelength or plural wavelengths, corresponding to the illumination optical system. Further, the detection optical system may have polarization transmission characteristics and detect only specific polarized light.

In the means for detecting a feature from the electrical signal, the feature may be the detected spectral data of each wavelength as it is, or may be a signal of one or more specific wavelengths. Further, the feature may be determined by a combination of plural polarized light conditions and wavelengths.

The comparison of a feature may be comparison in proximity on the same sample, comparison at a symmetrical position, comparison in area units by design information, and comparison with previously detected and stored data.

In the position detection means, with an image processing technique such as normalized correlation, a pattern arrangement in the design data (CAD data) and a distribution arrangement of the detected feature are compared to detect a position shift.

Figure 2:
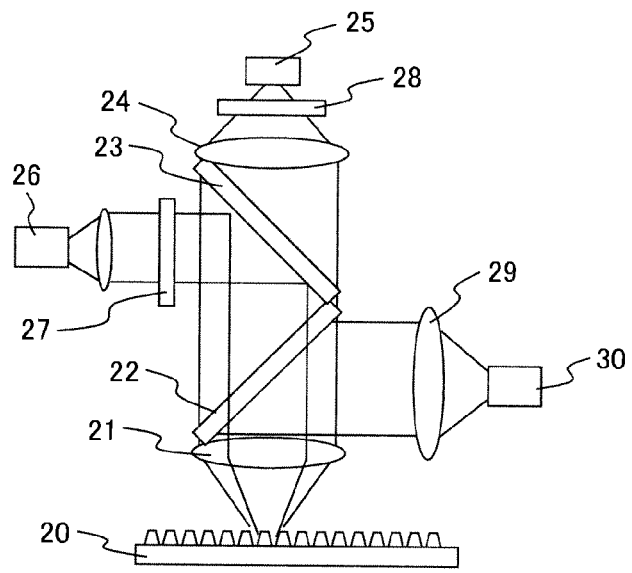
FIG. 2 is an illustration showing an optical system according to an embodiment of the invention.

FIG. 2 shows an example of the spectrometer 1. Light applied from a light source 26 through a polarizer 27 is reflected by a half mirror 23 and passes through a half mirror 22, and then a beam condensed by an objective lens 21 is applied to a patterned medium 20 to be inspected. The applied light is reflected on the patterned medium 20, passes through the objective lens 21, and is condensed by a condenser lens 24, and then a desired optical component is filtered by an analyzer 28 and detected by a light detector 25. In this case, for example if a white light source, a polarization plate, and a spectrometer are respectively used as the light source 26, the analyzer 28, and the light detector 25, a spectral waveform corresponding to the pattern shape and optical characteristics of the patterned medium 20 can be obtained. Such detection is performed on the whole surface of the patterned medium 20 as a sample, thereby making it possible to detect spectral waveforms on the whole surface of the sample. Further, light reflected by the half mirror 22 is condensed by a condenser lens 29 and captured by a camera 30, thereby making it possible to obtain a camera image of the same position as the spectral data acquired by the light detector 25.

Figure 3:
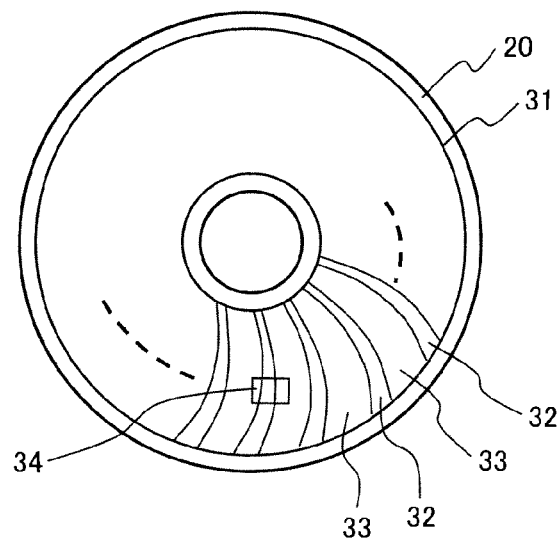
FIG. 3 is a general view of a patterned medium as an inspection sample.
Figure 4:
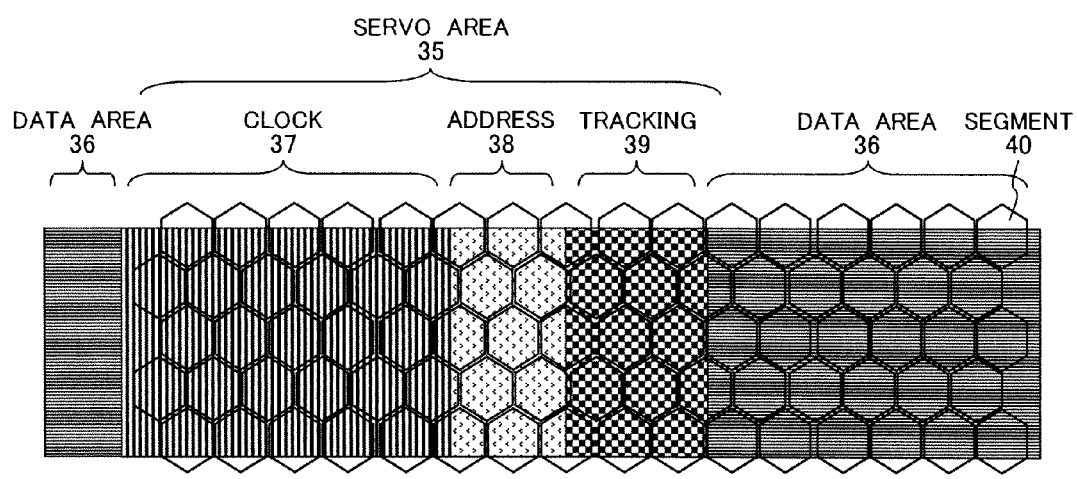
FIG. 4 is an enlarged detail view showing the patterned medium of FIG. 3.

With reference to FIG. 3, description will be made on a method of area segmentation and pattern classification in the case where the patterned medium 20 for an HDD is used as a sample. In the sample, an area 31 where a pattern is formed is an inspection area. In the HDD medium, servo areas 32 for controlling a head and data areas 33 for recording a user's magnetic data are formed radially. In the patterned medium for the HDD, a pre-servo method in which servo areas are formed as physical patterns is adopted. FIG. 4 is an enlarged view around a servo area. In a typical pattern arrangement, a servo area 35 is arranged between data areas 36, and composed of different patterns such as a clock area 37, an address area 38, and a tracking area 39 in accordance with magnetic signal application. A segment 40 represents a detection unit according to light sensor detection of the invention, and each area is segmented into detection units as shown in FIG. 4.

Figure 5:
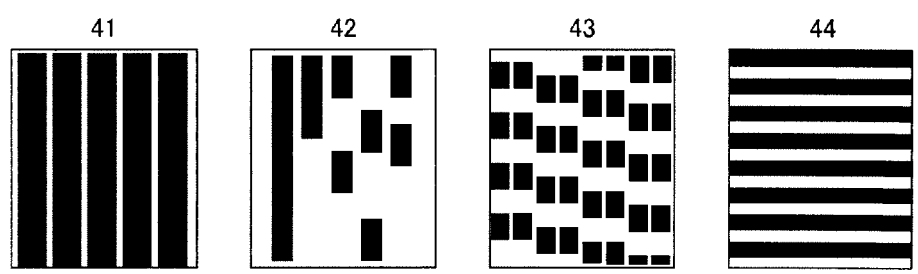
FIG. 5 is an enlarged detail view showing patterns of areas of FIG. 4.
Figure 6A:
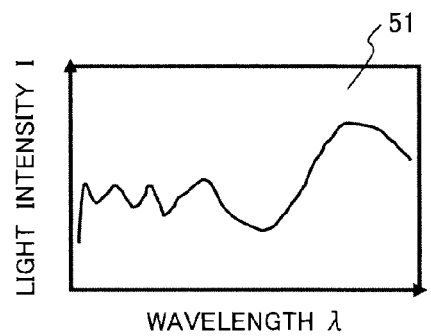
FIGS. 6A to 6D are graphs showing spectral waveforms of areas of FIG. 5.
Figure 6B:
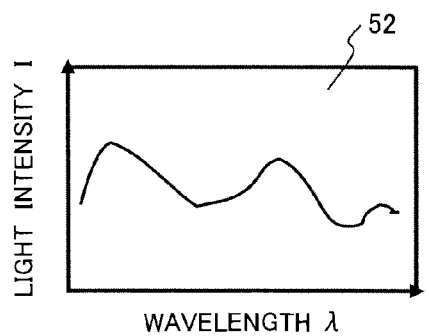
Figure 6C:
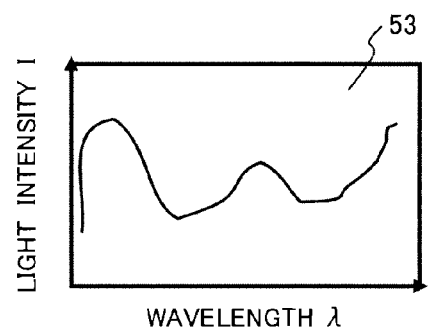
Figure 6D:
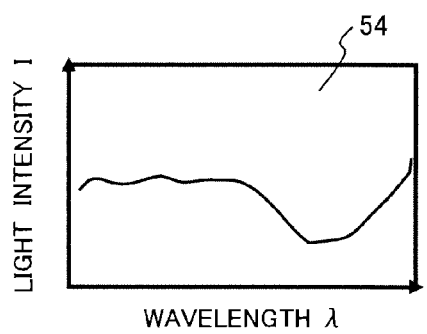

FIG. 5 shows pattern examples of the areas shown in FIG. 4. For example, a pattern 44 of the data area 36 is a periodic line-and-space pattern, a pattern 43 of the tracking area 39 is a periodic cross-stitch pattern, a pattern 42 of the address area 38 is a non-periodic pattern, and a pattern 41 of the clock area 37 is a periodic line-and-space pattern. FIGS. 6A to 6D show spectral waveforms of the respective areas detected by the light detector 25. A spectral waveform 51 of FIG. 6A shows a detection result of the data area 36 (pattern 44), a spectral waveform 52 of FIG. 6B shows a detection result of the tracking area 39 (pattern 43), a spectral waveform 53 of FIG. 6C shows a detection result of the address area 38 (pattern 42), and a spectral waveform 54 of FIG. 6D shows a detection result of the clock area 37 (pattern 41). Thus, the profiles of spectral waveforms vary greatly among different pattern shapes, so that it is possible to distinguish among patterns detected from the respective areas without recourse to position information.

Figure 7:
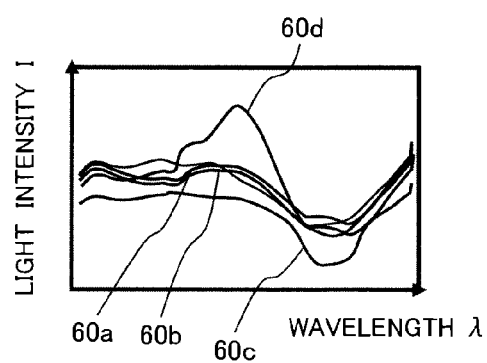
FIG. 7 is a graph showing spectral waveforms obtained by detecting four locations in a data area.
Figure 8:
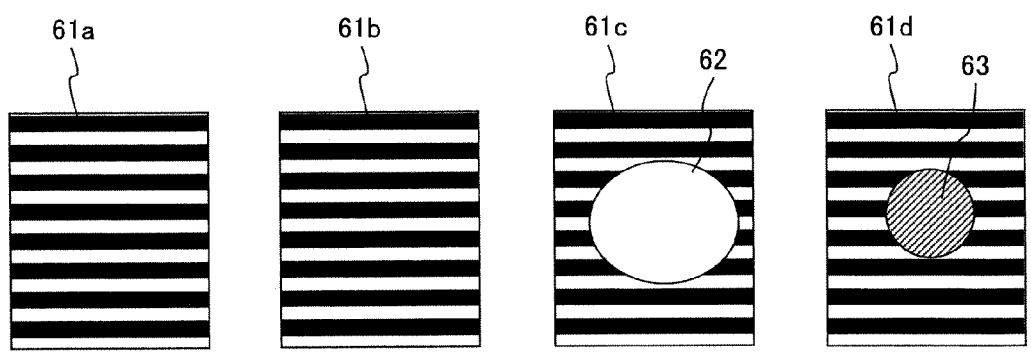
FIG. 8 is a view showing examples of the detected four locations in the data area.

FIG. 7 shows detection waveforms of four locations in the data area, and FIG. 8 shows pattern examples of the four locations. Detection waveforms 60a, 60b, 60c, and 60d of FIG. 7 correspond to pattern examples 61a, 61b, 61c, and 61d of FIG. 8, respectively. The pattern examples 61a and 61b show non-defective areas; therefore, there are only small changes in the waveforms 60a and 60b. This is because the data area is a periodic pattern so that there are only small changes in spectral waveforms regardless of location. On the other hand, there are large changes in the waveforms 60c and 60d obtained by detecting the area 61c including a pattern missing defect 62 and the area 61d including a particle defect 63. Further, the changing manner (change wavelength region) varies depending on the defect type.

Figure 9:
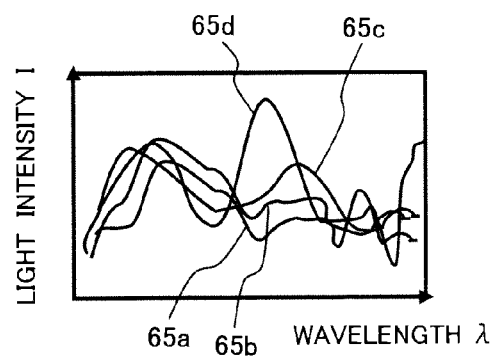
FIG. 9 is a graph showing spectral waveforms obtained by detecting four locations in an address area in a servo area.

FIG. 9 shows detection waveforms of four locations in the address area as a non-periodic pattern in the servo area. Detection waveforms 65a, 65b, 65c, and 65d of FIG. 9 correspond to pattern examples 66a, 66b, 66c, and 66d of FIG. 10, respectively. The pattern examples 66a and 66b show non-defective areas. Since the address area is not a uniform pattern, the detection waveforms 65a and 65b do not necessarily match. On the other hand, there are relatively large changes in the waveforms 65c and 65d obtained by detecting the area 66c including a pattern missing defect 67 and the area 66d including a particle defect 68. Further, the changing manner (change wavelength region) varies depending on the defect type.

Thus, the manner in which the spectral waveform changes varies depending on the detection area and the defect type, so that defect discrimination for each detection area is needed.

FIGS. 11A and 11B show an example of a determination database table necessary for feature calculation and determination processing. Here, spectral waveform data is represented as reflectance data with respect to each wavelength, that is, a function $f(\lambda k)$ of a wavelength $\lambda k$ ($k=1, 2, 3, \ldots$). The table of detection areas and defect types is prepared, and feature functions $F_i$ ($i=1, 2, 3, \ldots$) expressed by the following equation (1) and determination index values $T_{hi}$ ($i=1, 2, 3, \ldots$) are set in the table. Fi is a calculation equation obtained by multiplying reflected light intensities $f(\lambda k)$ at wavelengths of the spectral waveform by coefficients $\alpha, \beta, \gamma$ and so on.

$$F_i(\lambda) = \alpha \cdot f(\lambda_1) + \beta \cdot f(\lambda_2) + \gamma \cdot f(\lambda_3) + \ldots \quad (1)$$

where $F_i(\lambda)$ is a feature calculation equation, $f(\lambda k)$ is the reflectance value of the spectral waveform with respect to the wavelength $\lambda k$, $\alpha, \beta, \gamma \ldots$ are coefficients, $i=1, 2, 3 \ldots$, and $k=1, 2, 3$ and so on.

Samples whose detection areas and defect types are known are collected beforehand as teacher data, and each function Fi is determined based on the data of these spectral waveforms. Fi is determined by determining the coefficients $\alpha, \beta, \gamma$ and so on. For example, by comparing waveforms in an area, a coefficient of a wavelength of a large change depending on the defect type is increased, whereas a coefficient of a wavelength of a large change in a waveform of a non-defective product is decreased. These coefficients are determined in a statistical manner such as principal component analysis or PLS analysis technique. Further, a determination index value Thi for determining a defect type is set to a determined function value, and a detection waveform of a function value not less than the determination index value is determined to be the defect type.

While the calculation equation (1) is a linear equation for simplicity, it does not necessarily need to be a linear equation, and may be any other calculation equation as long as it has parameters of reflectance of spectral waveforms. For example, the calculation equation may be the following power equation (2).

$$F_i(\lambda) = \sum_{k=0}^{n} \{\alpha_k \cdot f(\lambda_k) + \beta_k \cdot f^2(\lambda_k) + \gamma_k \cdot f^3(\lambda_k) + ...\} \quad (2)$$

where $F_i(\lambda)$ is a feature calculation equation, $f(\lambda k)$ is the reflectance value of the spectral waveform with respect to the wavelength $\lambda k$, $\alpha k$, $\beta k$, $\gamma k$ ... are coefficients, i=1, 2, 3 ..., and k=1, 2, 3 and so on.

Further, the defect type of each area does not necessarily have to be determined by one determination index value Thi, and may be determined by a combination condition of plural index values.

The determination index value Thi is set by comparing an optical signal variation of a non-defective pattern with an optical signal change caused by a defect and capturing a significant signal change.

The determination equation and the database are thus constructed, thereby making it possible to detect and classify defects in each area.

Further, the defect type may be not only a physical change in pattern shape shown in this embodiment but also a magnetic defect type or an electrical defect type as long as it can be detected with a spectral waveform.

Second Embodiment

FIG. 12 shows an example of another determination database table according to the invention. In area setting in the first embodiment, the data area is divided into, for example, three areas in the radial direction of the disk, that is, inner, middle, and outer periphery areas. This is because, due to the nature of the hard disk, the recording density is higher toward the inner periphery, so that the pattern density may also vary depending on the radial position. In this case, it is not necessary to calculate the coefficients of the calculation equation Fi independently in all areas, and interpolation may be performed between adjacent areas. Further, the number of divisions is not limited to three and may be more than three.

Third Embodiment

FIGS. 13A and 13B show another example of a determination database according to the invention. When a spectral waveform is detected by the spectrometer 1 according to the first embodiment, a waveform 70 of FIG. 13A detected by the light detector 25 and a defect image 71 of FIG. 13B captured by the camera 30 are associated together and stored in the database. This makes it possible to show the defect image 71 to a user as a defect image example after determination.

The invention claimed is:

1. A method for determining a defect in a fine concave-convex pattern when a feature of an inspection object is detected via scatterometry in inspection of the fine concave-convex pattern, the method comprising:
   a) detecting a spectral waveform of a detection area of the inspection object;
   b) performing an area determination to determine an area section to which the detection area belongs based on a pattern type of the inspection object in accordance with design information or the spectral waveform;
   c) selecting a feature calculation equation and at least one determination index value corresponding to the determined area section, based on a result of the area determination;
   d) performing feature calculation on data for the detected spectral waveform in accordance with the selected feature calculation equation;
   e) comparing a calculated feature value with the at least one selected determination index value to perforin determination processing; and
   f) performing defect type determination based on a result of determination processing.

2. The method for determining a defect in a fine concave-convex pattern according to claim 1, wherein performing the area determination comprises classifying the pattern type of the inspection object into a periodic pattern and a non-periodic pattern.

3. The method for determining a defect in a fine concave-convex pattern according to claim 1, wherein performing determination processing comprises:
   comparing, when an optical signal changes depending on the pattern type of the inspection object and the defect type, an optical signal variation of a non-defective pattern and an optical signal change caused by a defect, and capturing a significant signal change.

4. The method for determining a defect in a fine concave-convex pattern according to claim 3, comprising:
   selecting a wavelength based at least in part on an amplitude of the wavelength, and
   determining a defect based on the amplitude of the selected wavelength.

5. The method for determining a defect in a fine concave-convex pattern according to claim 1, comprising selecting a predetermined determination index value according to pattern type based on the area determination.

6. The method for determining a defect in a fine concave-convex pattern according to claim 1, wherein the feature calculation equation is:

$$F_i(\lambda) = \alpha \cdot f(\lambda_1) + \beta \cdot f(\lambda_2) + \gamma \cdot f(\lambda_3) + ...$$

where $F_i(\lambda)$ is the feature calculation equation, $f(\lambda k)$ is a reflectance value of the spectral waveform with respect to a wavelength $\lambda k$, $\alpha$, $\gamma$ ... are coefficients, i=1, 2, 3 ..., and k=1, 2, 3 ....

7. The method for determining a defect in a fine concave-convex pattern according to claim 1, wherein the feature calculation equation is:

$$F_i(\lambda) = \sum_{k=0}^{n} \{\alpha_k \cdot f(\lambda_k) + \beta_k \cdot f^2(\lambda_k) + \gamma_k \cdot f^3(\lambda_k) + ...\}$$

where $F_i(\lambda)$ is the feature calculation equation, $f(\lambda k)$ is a reflectance value of the spectral waveform with respect to a wavelength $\lambda k$, $\alpha k$, $\beta k$, $\gamma k$ ... are coefficients, i=1, 2, 3 ..., and k=1, 2, 3 ....

8. A method for determining a defect on a patterned medium via scatterometry, the method comprising:
   a) detecting a spectral waveform of a detection area of a patterned medium;
   b) performing an area determination to determine an area section to which the detection area belongs based on a pattern type of the patterned medium in accordance with design information or the spectral waveform;

c) selecting a feature calculation equation and at least one determination index value corresponding to the determined area section, based on a result of the area determination;

d) performing feature calculation on data for the detected spectral waveform in accordance with the selected feature calculation equation;

e) comparing a calculated feature value with the at least one selected determination index value to perform determination processing; and f) performing defect type determination based on a result of determination processing.

9. The method for determining a defect on a patterned medium according to claim 8, wherein the defect type includes a void, a foreign substance, and a scratch.

10. The method for determining a defect on a patterned medium according to claim 8, wherein the area section includes a data area and a servo area.

11. The method for determining a defect on a patterned medium according to claim 10, wherein the data area in the area section is divided into an inner periphery area, a middle periphery area, and an outer periphery area.

12. The method for determining a defect on a patterned medium according to claim 10, wherein the servo area in the area section is divided into an address area, a clock area, and a tracking area.

* * * * *